United States Patent
Razavi et al.

(10) Patent No.: US 7,034,157 B2
(45) Date of Patent: Apr. 25, 2006

(54) CATALYST COMPONENTS, PROCESS FOR THEIR PREPARATION AND THEIR USE AS CATALYST COMPONENTS IN POLYMERIZATION OF OLEFINS

(75) Inventors: Abbas Razavi, Mons (BE); Vladimir Marin, Houston, TX (US); Margarito Lopez, Pasadena, TX (US)

(73) Assignee: Fina Technology, Inc., Houston, TX (US)

(*) Notice: Subject to any disclaimer, the term of this patent is extended or adjusted under 35 U.S.C. 154(b) by 59 days.

(21) Appl. No.: 10/691,810

(22) Filed: Oct. 23, 2003

(65) Prior Publication Data

US 2005/0090385 A1    Apr. 28, 2005

(51) Int. Cl.
   *C07F 15/00*     (2006.01)
   *C07F 15/02*     (2006.01)
   *B01J 31/00*     (2006.01)

(52) U.S. Cl. .............. 546/2; 546/10; 556/32; 556/33; 556/34; 556/35; 556/137; 556/138; 556/140; 502/159; 502/160; 502/162; 502/167

(58) Field of Classification Search ........... 502/159, 502/160, 162, 167; 556/32–35, 137, 138, 556/140; 546/2, 10
See application file for complete search history.

(56) References Cited

U.S. PATENT DOCUMENTS

| | | |
|---|---|---|
| 4,404,344 A | 9/1983 | Sinn et al. |
| 4,767,735 A | 8/1988 | Ewen et al. |
| 5,155,080 A | 10/1992 | Elder et al. |
| 5,387,568 A | 2/1995 | Ewen et al. |
| 5,807,939 A | 9/1998 | Elder et al. |
| 5,945,365 A | 8/1999 | Reddy |
| 6,150,482 A | 11/2000 | Brookhart et al. |

(Continued)

FOREIGN PATENT DOCUMENTS

CN     1352204 A  *  6/2001

(Continued)

OTHER PUBLICATIONS

Changkun Liu et al., New J. Chemistry, vol. 26, no. 10, pp. 1485-1489 (2002).*

(Continued)

*Primary Examiner*—J. A. Lorengo
*Assistant Examiner*—J. Pasterczyk
(74) *Attorney, Agent, or Firm*—William D. Jackson; Tenley R. Krueger

(57) ABSTRACT

Olefin polymerization catalyst precursors are described herein. The precursors are generally characterized by the formula:

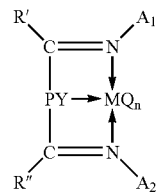

wherein M is a transition metal selected from groups 8 to 10 of the Periodic Table; n is an integer of from 1 to 3; Q is a halogen or a $C_1$ to $C_2$ alkyl group; PY is a pyridinyl group, which is coordinated with M through the nitrogen atom of said pyridinyl group; R' is a $C_1$ to $C_{20}$ hydrocarbyl group; R" is a $C_1$ to $C_{20}$ hydrocarbyl group; $A_1$ is a monoaromatic group, which is substituted or unsubstituted; and $A_2$ includes multiple aromatic groups, which are substituted or unsubstituted.

20 Claims, 1 Drawing Sheet

U.S. PATENT DOCUMENTS

| | | |
|---|---|---|
| 6,313,242 B1 | 11/2001 | Reddy |
| 6,365,690 B1 * | 4/2002 | Lenges ................. 526/172 |
| 6,414,098 B1 | 7/2002 | Engehausen et al. |
| 6,545,075 B1 | 4/2003 | Nishihata et al. |
| 2003/0119921 A1 * | 6/2003 | De Boer et al. ............ 518/715 |
| 2004/0039238 A1 * | 2/2004 | Zhao et al. ................ 585/513 |
| 2005/0159601 A1 * | 7/2005 | De Boer et al. ............... 546/2 |

FOREIGN PATENT DOCUMENTS

| | | | |
|---|---|---|---|
| CN | 1306012 A | * | 8/2001 |
| CN | 1306013 A | * | 8/2001 |
| CN | 1371923 A | * | 10/2002 |
| EP | 1125928 A1 | | 8/2001 |
| WO | WO 99/12981 | | 3/1999 |

OTHER PUBLICATIONS

Changkun Liu et al., "Polymerized Unsymmetrical Iron Post-Metallocene Catalyst for Ethylene Polymerization", Huaxue Xuebao (2002), vol. 60, no. 1, pp. 157-161 (2002) (Chem. Abstracts 136:325871).*

Brooke L. Small, Tridentate Cobalt Catalysts for Linear Dimerization and Isomerization of Alpha-Olefins, Organometallics, 2003, pp. 3178-3183, 2003.

* cited by examiner

FIG. 1

CATALYST COMPONENTS, PROCESS FOR THEIR PREPARATION AND THEIR USE AS CATALYST COMPONENTS IN POLYMERIZATION OF OLEFINS

FIELD OF THE INVENTION

This invention relates to olefin polymerization catalysts and their preparation and use in the polymerization of ethylenically unsaturated monomers.

BACKGROUND OF THE INVENTION

Olefin polymers such as polyethylene, polypropylene, which may be atactic or stereospecific, such as isotactic or syndiotactic, and ethylene-higher alpha olefin copolymers, such as ethylene-propylene copolymers can be produced under various polymerization conditions and employing various polymerization catalysts. Such polymerization catalysts include Ziegler-Natta catalysts and non-Ziegler-Natta catalysts, such as metallocenes and other transition metal catalysts which are typically employed in conjunction with one or more co-catalysts. The polymerization catalysts may be supported or unsupported.

The alpha olefin homopolymers or copolymers may be produced under various conditions in polymerization reactors which may be batch type reactors or continuous reactors. Continuous polymerization reactors typically take the form of loop-type reactors in which the monomer stream is continuously introduced and a polymer product is continuously withdrawn. For example, polymers such as polypropylene, polyethylene or ethylene-propylene copolymers involve the introduction of the monomer stream into the continuous loop-type reactor along with an appropriate catalyst system to produce the desired olefin homopolymer or copolymer. The resulting polymer is withdrawn from the loop-type reactor in the form of a "fluff" which is then processed to produce the polymer as a raw material in particulate form as pellets or granules. In the case of $C_{3+}$ alpha olefins, such a propylene or substituted ethylenically unsaturated monomers such as styrene or vinyl chloride, the resulting polymer product may be characterized in terms of stereoregularity, such as in the case of, for example, isotactic polypropylene or syndiotactic polypropylene. Other unsaturated hydrocarbons which can be polymerized or copolymerized with relatively short chain alphaolefins, such as ethylene and propylene include dienes, such as 1,3-butadiene or 1,4-hexadiene or acetylenically unsaturated compounds, such as methylacetylene.

SUMMARY OF THE INVENTION

In accordance with the present invention, there are provided catalyst compositions and processes for the polymerization of ethylenically unsaturated monomers to produce polymers, including copolymers or homopolymers. Monomers, which are polymerized or copolymerized in accordance with the present invention, include ethylene, $C_{3+}$ alphaolefins and substituted vinyl compounds, such as styrene and vinyl chloride. A further application of the present invention is in the polymerization of $C_{4+}$ conjugated dienes including specifically, butadiene. A particularly preferred application of the invention is in the polymerization of ethylene including the homopolymerization of ethylene to produce polyethylene, and the copolymerization of ethylene and a $C_{3+}$ alphaolefin to produce an ethylene alphaolefin copolymer, specifically an ethylene-propylene copolymer.

In carrying out the present invention, there is provided an olefin polymerization catalyst composition comprising a Cs symmetric catalyst component characterized by the formula:

(I)

In formula (I), M is a Group 4-11 transition metal, n is an integer within the range of 1–3, Q is a halogen or a $C_1$–$C_2$ alkyl group, and PY is a pyridinyl group which is coordinated with M through the nitrogen atom of the pyridinyl group. Further, with respect to formula (I), R' and R" are each independently a $C_1$–$C_{20}$ hydrocarbyl group, $A_1$ is a mononuclear aromatic group, which may be substituted or unsubstituted, and $A_2$ is a polynuclear aromatic group, which may be substituted or unsubstituted.

In a preferred embodiment of the invention, R' and R" are each independently a $C_1$–$C_4$ alkyl group or a substituted or unsubstituted mononuclear aryl group. Preferably, M is a transition metal selected from Groups 8-10 of the Periodic Table and more specifically, iron or cobalt, with n being 2. $A_1$ may take the form of an unsubstituted phenyl group or a substituted phenyl group which is mono-substituted, di-substituted or tri-substituted. In one embodiment of the invention, $A_1$ is a phenyl group which is mono-substituted at the directly distal position with respect to the coordinating nitrogen atom. In a further application of the invention, $A_1$ is a di-substituted phenyl group substituted at the proximal positions with a $C_1$–$C_4$ alkyl group, each alkyl group being the same, or a tri-substituted phenyl group substituted with the same $C_1$–$C_4$ alkyl groups at the proximal positions and substituted with a $C_1$–$C_4$ alkyl group at the directly distal position, which may the same or different from the alkyl substituents at the proximal positions. Preferably, the ligand component $A_2$ is a substituted or unsubstituted terphenyl group. In one embodiment, the primary benzyl group of the terphenyl group is substituted with the substituent phenyl groups thereof at the proximal positions with respect to the coordinating nitrogen ion. In a further embodiment of the invention, both of the substituent phenyl groups of the terphenyl group are substituted at the para-positions with $C_1$–$C_4$ alkyl groups.

In a preferred embodiment of the invention, M is a transition metal selected from the group consisting of iron, cobalt, nickel and copper. Preferably, M is iron or cobalt and more specifically, iron. In this case, the Cs symmetric catalyst component is characterized by the formula:

(II)

In formula (II), M is iron, cobalt, nickel or copper and $A_1$ and $A_2$ are aromatic groups with $A_1$ being a substituted or unsubstituted aromatic group and $A_2$ being a substituted aromatic group which is sterically different from $A_1$. PY is a pyridinyl group and Q is a halogen or a $C_1$–$C_2$ alkyl group as described previously.

A specific embodiment of the present invention in which the coordinating transition metal is iron, is a catalyst component having Cs symmetry, which is characterized by the following formula:

(III)

In formula (III), Q is a hydrogen or a $C_1$–$C_2$ alkyl group and the substituents $R_1$ and $R_2$ on the phenyl group are, respectively, hydrogen or a $C_1$–$C_4$ alkyl group and a $C_1$–$C_4$ alkyl group. With regard to the substituents on the terphenyl group of formula (III), $R_3$ is a hydrogen or a $C_1$–$C_4$ alkyl group, and $R_5$ is hydrogen or a $C_1$–$C_4$ alkyl group which can be the same as or different from $R_3$. The distal constituents, $R_4$, are each hydrogen or a $C_1$–$C_4$ alkyl group with $R_4$ and are the same substituents. Specific catalyst components are characterized by the catalyst component of formula (III) in which $R_2$ is an isopropylene group and each $R_4$ is hydrogen.

In yet a more specific embodiment of the invention, the Cs symmetric catalyst component is characterized by the formula:

(IV)

In formula (IV), Q is a halogen or a $C_1$–$C_2$ alkyl group, $R_1$ is a hydrogen or methyl group, and $R_2$ is a methyl or ethyl group. The distal substituents, $R_4$ on the terphenyl group, are the same and are each a $C_2$–$C_4$ alkyl group having a higher molecular weight than $R_2$. More specifically, the substituents $R_2$ are each a methyl group and the substituents $R_4$ are each isopropyl or tertiary butyl groups. Preferably, the substituents $R_4$ are tertiary butyl groups, $R_1$ is a methyl group and Q is chlorine.

In a further embodiment of the present invention, there are provided processes for the polymerization of one or more ethylenically unsaturated monomers to produce a corresponding homopolymer or copolymer. In carrying out the polymerization process of the present invention, there is provided a transition metal catalyst component having Cs symmetry as characterized by formula (I) above and, more specifically, by the following structural formula:

(V)

In formula (V), M is a transition metal selected from Group 8-10 of the Periodic Table and Q, $R_1$, $R_2$, $R_4$ and $R_5$ are as described above with respect to formula (III).

In addition to the transition metal catalyst component, there is provided an activating co-catalyst component such as an alumoxane. The catalyst component and the co-catalyst component are contacted in a polymerization reaction zone with an ethylenically unsaturated monomer under polymerization conditions to produce a polymer product which is then recovered from the reaction zone. Preferably, the activating co-catalyst comprises methylalumoxane (MAO) or tri-isobutylalumoxane (TIBAO) or mixtures thereof. Alternatively, the activating co-catalyst can take the form of a noncoordinating anionic type, such as triphenylcarbenium tetrakis(pentafluorophenyl)aluminate or triphenylcarbenium tetrakis(pentafluorophenyl)boronate.

In yet a further aspect of the invention, there is provided a process for the preparation of a pyridinyl-linked bis-amino ligand suitable for use in forming the catalyst component of the present invention. In carrying out this aspect of the invention, 2,6-dibromophenyl amine is reacted with an arylboronic acid which is substituted or unsubstituted to produce a corresponding 2,6-diarylphenyl amine which is substituted or unsubstituted. The 2,6-diarylphenyl amine is reacted with dialkanoic pyridine characterized by the formula:

(VI)

In formula (VI), R' and R" are each independently a $C_1$–$C_{20}$ alkyl group.

The reaction product is a mono-imine ligand characterized by the formula:

(VII)

In formula (VII), TRP is a terphenyl group, which is substituted or unsubstituted.

The mono-imine ligand is reacted with a substituted or unsubstituted aniline to produce a bis-imine ligand characterized by the formula:

(VIII)

wherein TRP is as described above and AR is a substituted or unsubstituted aryl group.

DETAILED DESCRIPTION OF INVENTION

The present invention involves pyridinyl-bridged transition metal catalysts having Cs symmetry and their preparation and use in the polymerization of olefins. Specific olefins which may be polymerized, either through homopolymerization or copolymerization include ethylene, propylene, butylene and conjugated dienes such as 1,3-butadiene, as well as monoaromatic or substituted vinyl compounds as described previously. The Cs symmetric catalyst components of the present invention incorporate transition metals from Groups 4-11 of the Periodic Table of Elements (new notation) and more particularly, transition metals from Groups 8-11 of the Periodic Table of Elements. Preferred transition metals for use in the catalyst components of the present invention are iron, cobalt, nickel and copper with iron and cobalt being particularly preferred.

The catalyst components of the present invention incorporate pyridinyl-linked bis-amino ligand structures which are unbalanced and incorporate a mononuclear aromatic group linked to one nitrogen atom and a polynuclear aromatic group linked to the other nitrogen atom. The mononuclear and polynuclear aromatic groups may be substituted or unsubstituted, but if substituted, each aromatic group is symmetrical with respect to each group's respective coordinating nitrogen atom. Thus, the catalyst component incorporates a ligand structure having Cs symmetry. The plane of symmetry extends through the transition metal and to nitrogen atoms of the bis-amino ligand as shown by the following diagram of a bridged phenyl-terphenyl structure as indicated below:

(IX)

In diagram (IX), the plane of symmetry is indicated by the broken line and is perpendicular to the plane of the paper in which the phenyl and terphenyl groups are schematically shown. With respect to the phenyl group, Cs symmetry is observed if the phenyl group is unsubstituted, mono-substituted at the 4 (directly distal position), di-substituted at the 2,6 positions with the same substituents, or at the 3,5 positions with the same substituents. With respect to the terphenyl group, Cs symmetry is maintained if the terphenyl group is unsubstituted, di-substituted at the distal positions 4 and 4' of the substituent phenyl groups, or substituted on the substituent phenyl groups at the 2 and 2' positions with the same substituent groups, and at the 6 and 6' positions with the same substituent groups, which may be the same or different than the substituents at the 2 and 2' positions. Diagram (IX), which schematically shows a phenyl-terphenyl ligand structure in which the substituent phenyl groups are substituted on the primary benzyl group of the terphenyl group at the proximal positions with respect to the nitrogen linkage, is illustrative of embodiments of the invention such as shown by formulas (III), (IV) and (V) above.

In employing the catalyst components of the present invention in polymerization procedures, they are used in conjunction with an activating co-catalyst. Suitable activating co-catalysts may take the form of co-catalysts such are commonly employed in metallocene-catalyzed polymerization reactions. Thus, the activating co-catalyst may take the form of an aluminum co-catalyst. Alumoxane co-catalysts are also referred to as aluminoxane or polyhydrocarbyl aluminum oxides. Such compounds include oligomeric or polymeric compounds having repeating units of the formula:

(X)

where R is an alkyl group generally having 1 to 5 carbon atoms. Alumoxanes are well known in the art and are generally prepared by reacting an organo-aluminum compound with water, although other synthetic routes are known to those skilled in the art. Alumoxanes may be either linear polymers or they may be cyclic, as disclosed for example in U.S. Pat. No. 4,404,344. Thus, alumoxane is an oligomeric or polymeric aluminum oxy compound containing chains of alternating aluminum and oxygen atoms whereby the aluminum carries a substituent, preferably an alkyl group. The structure of linear and cyclic alumoxanes is generally believed to be represented by the general formula —(Al(R)—O—)-m for a cyclic alumoxane, and $R_2Al$—O—(Al(R)—O)m-$AlR_2$ for a linear compound wherein R independently each occurrence is a $C_1$–$C_{10}$ hydrocarbyl, preferably alkyl or halide and m is an integer ranging from 1 to about 50, preferably at least about 4. Alumoxanes also exist in the configuration of cage or cluster compounds. Alumoxanes are typically the reaction products of water and an aluminum alkyl, which in addition to an alkyl group may contain halide or alkoxide groups. Reacting several different aluminum alkyl compounds, such as, for example, trimethylaluminum and tri-isobutylaluminum, with water yields so-called modified or mixed alumoxanes. Preferred alumoxanes are methylalumoxane and methylalumoxane modified with minor amounts of other higher alkyl groups such as isobutyl. Alumoxanes generally contain minor to substantial amounts of the starting aluminum alkyl compounds. The preferred co-catalyst, prepared either from trimethylaluminum or tri-isobutylaluminum, is sometimes referred to as poly (methylaluminum oxide) and poly (isobutylaluminum oxide), respectively.

The alkyl alumoxane co-catalyst and transition metal catalyst component are employed in any suitable amounts to provide an olefin polymerization catalyst. Suitable aluminum transition metal mole ratios are within the range of 10:1 to 20,000:1 and preferably within the range of 100:1 to 5,000:1. Normally, the transition metal catalyst component and the alumoxane, or other activating co-catalyst as described below, are mixed prior to introduction in the polymerization reactor in a mode of operation such as described in U.S. Pat. No. 4,767,735 to Ewen et al. The polymerization process may be carried out in either a batch-type, continuous or semi-continuous procedure, but preferably polymerization of the olefin monomer (or monomers) will be carried out in a loop type reactor of the type disclosed in the aforementioned U.S. Pat. No. 4,767,735. Typical loop type reactors include single loop reactors or so-called double loop reactors in which the polymerization procedure is carried in two sequentially connected loop reactors. As described in the Ewen et al. patent, when the catalyst components are formulated together, they may be supplied to a linear tubular pre-polymerization reactor where they are contacted for a relatively short time with the pre-polymerization monomer (or monomers) prior to being introduced into the main loop type reactors. Suitable contact times for mixtures of the various catalyst components prior to introduction into the main reactor may be within the range of a few seconds to 2 days. For a further description of suitable continuous polymerization processes which may be employed in carrying out the present invention, reference is made to the aforementioned U.S. Pat. No. 4,767,735, the entire disclosure of which is incorporated herein by reference.

Other suitable activating co-catalysts which can be used in carrying out the invention include those catalysts which function to form a catalyst cation with an anion comprising one or more boron atoms. By way of example, the activating co-catalyst may take the form of triphenylcarbenium tetrakis (pentafluorophenyl) boronate as disclosed in U.S. Pat. No. 5,155,080 to Elder et al. As described there, the activating co-catalyst produces an anion which functions as a stabilizing anion in a transition metal catalyst system. Suitable noncoordinating anions include $[W(PhF_5)]^-$, $[Mo(PhF_5)]^-$ (wherein P $F_5$ is pentafluorophenyl), $[ClO_4]^-$, $[S_2O_6]^-$, $[PF_6]^-$, $[SbR_6]^-$, $[AlR_4]^-$ (wherein each R is independently Cl, a $C_1$–$C_5$ alkyl group preferably a methyl group, an aryl group, e.g. a phenyl or substituted phenyl group, or a fluorinated aryl group). Following the procedure described in the Elder et al. patent, triphenylcarbenium tetrakis(pentafluorophenyl) boronate may be reacted with pyridinyl-linked bis-amino ligand of the present invention in a solvent, such as toluene, to produce a coordinating cationic-anionic complex. For a further description of such activating co-catalyst, reference is made to the aforementioned U.S. Pat. No. 5,155,080, the entire disclosure of which is incorporated herein by reference.

In addition to the use of an activating co-catalyst, the polymerization reaction may be carried out in the presence of a scavenging agent or polymerization co-catalyst which is added to the polymerization reactor along with the catalyst component and activating co-catalyst. These scavengers can be generally characterized as organometallic compounds of metals of Groups IA, IIA, and IIIB of the Periodic Table of Elements. As a practical matter, organoaluminum compounds are normally used as co-catalysts in polymerization reactions. Specific examples include triethylaluminum, tri-isobutylaluminum, diethylaluminum chloride, diethylaluminum hydride and the like. Scavenging co-catalysts normally employed in the invention include methylalumoxane (MAO), triethylaluminum (TEAL) and tri-isobutylaluminum (TIBAL).

The process for the preparation of the pyridinyl ligand can be exemplified by the preparation of the following ligand:

(XI)

The procedure of preparing the above ligand comprises the following reactions:

(a) preparation of 2,6-diarylphenyl amine by the reaction of 2,6-dibromophenylamine and arylboronic acid as follows:

(XII)

(b) reacting the 2,6-diarylphenyl amine with 2,6-diacethyl pyridine with the presence of p-toluenesulfonic acid in toluene to form a mono-imine ligand as indicated below:

(XIII)

(c) reacting the mono-imine ligand with an aniline or substituted aniline with the presence of p-toluenesulfonic acid in toluene to form an Cs-symmetric bis-imine ligand as follows:

(XIV)

8

The ligands produced by reactions (XII–XIV), according to the present invention, are prepared by means of a very simple and efficient process, which employs inexpensive starting materials and comprises single reaction steps having high yields. Furthermore, this process does not require laborious and time-consuming purification procedures, and thus is particularly suitable to large-scale production.

The initial procedure (a) comprises reacting dibromoaniline with at least 2 equivalents and preferably 2–3 equivalents of the arylboronic acid. This reaction is carried out in the presence of a palladium catalyst, preferably Pd(PPh$_3$)$_4$, and with at least 0.5 mol %, and preferably 0.5–5.0 mol % of palladium catalyst, and in the presence of at least 3 equivalents of Na$_2$CO$_3$ or K$_2$CO$_3$, preferably 3–7 equivalents of Na$_2$CO$_3$ or K$_2$CO$_3$. According to a preferred embodiment of the process of the invention, reaction (a) is carried out in the presence of toluene, alcohol and water, preferably in ratio 10: (1-2): (1-0.1). The initial reaction is preferably carried out at a temperature ranging from 20° to 150° C. for a time of 1–24 hours, and more preferably for 2–3 hours. The resulting amine product can be isolated by crystallization or by column chromatography.

Reaction (b) comprises reacting 2,6-diacetylpyridine (4) with at least 1 equivalent and preferably 1.0–1.2 equivalents of the diarylaniline (3) product of reaction (b), to obtain the intermediate compound of formula (6). Reaction (b) is carried out in the presence of an acid as a catalyst, preferably p-toluenesulfonic acid, in an organic solvent such as alcohol, aliphatic or aromatic solvents, preferably in benzene or toluene. Reaction (b) is preferably carried out at a temperature ranging from 20° to 150° C., preferably 80° to 120° C. for a time of 1–72 hours, and more preferably for 5–12 hours. The obtained intermediate compound of formula (6) can be isolated by crystallization or used without isolation for reaction (c).

Reaction (c) comprises reacting the intermediate compound of formula (6) with at least 1 equivalent and preferably 1.0–1.2 equivalents of the diarylaniline of formula (7) prepared in reaction (b) to obtain the intermediate compound of formula (8). This reaction is carried out in the presence of an acid as a catalyst, preferably p-toluenesulfonic acid, in an organic solvent such as alcohol, aliphatic or aromatic sol- vents, preferably in benzene or toluene. Reaction (c) is preferably carried out at a temperature ranging from 20° to 150° C., preferably 80° to 120° C. for a time of 1–72 hours, and more preferably for 5–12 hours. The resulting compound of formula (8) can be isolated by crystallization.

Another synthesis sequence which can be used to make the desired ligand of formula (8) involves reaction (a) as described above and alternative reactions (b') and (c') as described below. Reaction (b') comprises reacting 2,6-diacetylpyridine (4) with at least 1 equivalent and preferably 1.0–1.2 equivalents of diarylaniline (7) to obtain the intermediate compound of formula (9):

Alternative reaction step (c') comprises reacting the intermediate compound of formula (9) with at least 1 equivalent and preferably 1.0–1.2 equivalents of the diarylaniline of formula (3) prepared in reaction (a):

8

While this alternative sequence is effective, the original sequence described above will usually be preferred. In this regard, the reaction of compound of formula (9) with compound of formula (3) resulted in the desired product (8) along with several side products due to a reversible condensation process of the imine formation. Therefore in sequences of the ligand synthesis the attachment of the bulkier aniline is preferably the first reaction.

The ligand of formula (8) according to the present invention can be readily transformed into corresponding catalyst component by reaction with MCl$_n$, e.g. where M is Fe or Co and n is 2, by using standard procedures disclosed in U.S. Pat. No. 6,414,098 to Engchausen et al., the entire disclosure of which is incorporated herein by reference, and also in B. L. Small, Organometallics, vol. 22, p. 3178 (2003):

(XVII)

10

As noted previously, the Cs symmetric compounds of the present invention can be used as catalytic components for the polymerization of olefins. The catalysts used for the polymerization of olefins include the product obtainable by contacting the follow components:

(1) one or more Cs symmetric compounds as described above or mixture of such Cs symmetric compounds with a nonmetallocene or metallocene catalysts, and (2) a suitable activating cocatalyst.

As noted previously, activating co-catalysts suitable as component (2) in catalysts of the invention are linear, branched or cyclic alumoxane, containing at least one group of the type:

(XVIII)

wherein the substituents R$_a$ and R$_b$ are the same or different from each other and are C$_1$–C$_{20}$ alkyl, C$_5$–C$_{20}$ cycloalkyl, C$_6$–C$_{20}$ aryl, or groups —O—Al(R). Examples of alumoxanes suitable as activating co-catalysts according to present invention are methylalumoxane (MAO), tetra-isobutylalumoxane (TIBAO) and mixtures of different alumoxanes (MMAO). Activating co-catalysts suitable for use in the invention can be produced from trialkylaluminum compounds by reaction with water as described above. Further activating co-catalysts suitable for use in the invention include compounds capable of forming an alkyl catalyst cation of formula X$^+$Y$^-$ as disclosed above. The Y$^-$ anion preferably comprises one or more boron atoms. More preferably, the Y$^-$ anion is an anion of formula BAr$^-$, where Ar substituents, which are the same or different, are aryl groups as phenyl or pentafluorophenyl.

The polymerization process of the present invention involves the polymerization of one or more olefinic monomers in the presence of a catalyst as described above. Representative examples of olefinic monomers which may be used in the polymerization process are ethylene, α-olefins such as propylene and 1-butene, and conjugated di-olefins. The catalysts of the invention can be advantageously used in ethylene homopolymerization. Unexpectedly high yields at 80° C. are achieved of ethylene polymers having advantageous properties for different polymer applications, for example, for medium density films.

Figure 1:
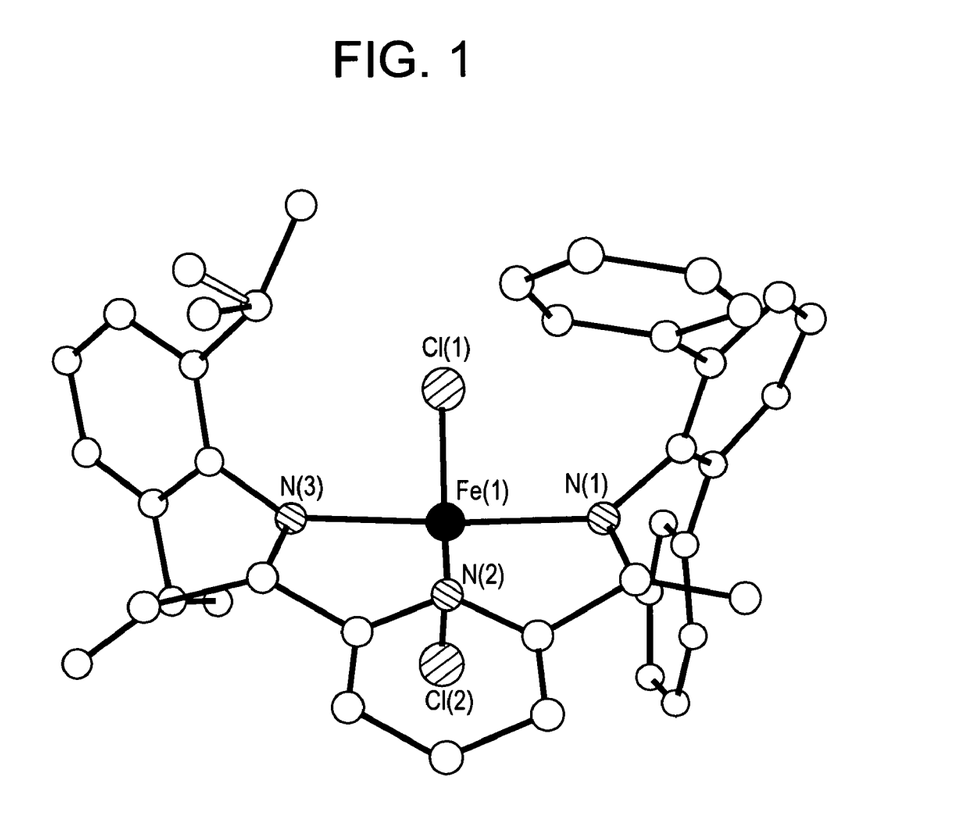
The drawing is a perspective view of a Cs symmetric catalyst component produced in accordance with the present invention.

The high stability of the catalysts under polymerization process at 80° C. and a high Mw of polyethylenes produced may be explained in terms of specific structural features of the catalysts of the invention. The structure of a Cs symmetric compound as determined by X-ray analysis of a single crystal is indicated by the perspective structural formula of FIG. 1. Table 1 summarizes the data of the selected angles in degrees and bond lengths in Angstroms for this Cs symmetric catalyst component and for a corresponding C2v symmetric catalyst. As indicated by the x-ray data, the Cs symmetric catalyst component contains bulkier aromatic groups at the 2,6-position of phenyl rings of imino-group, which change the geometry of the catalysts component to give more stable catalytic species during the polymerization process, and therefore the catalyst system produces polyethylene polymers more efficiently at higher temperatures.

TABLE 1

|  | C2v complex bis-[(2,6-diiso-propylphenyl-iminoethyl] pyridine iron dichloride* | Cs complex 2-[1-(2,6-diisopropyl-phenylimino(ethyl]-6-[1-(2,6-diphenyl phenylimino)ethyl] pyridine iron dichloride |
|---|---|---|
| Fe—N(imine) | 2.222, 2.225 | 2.232; 2.287 |
| Fe—N(pyridine) | 2.091 | 2.074 |
| N(imine)-C(L) | 1.437; 1.461 | 1.449; 1.451 |
| N=C | 1.295; 1.301 | 1.288; 1.294 |
| N(imine)-Fe—N(imine) | 140.2 | 143.7 |
| Fe—N(imine)-C(L) | 125.6; 124.9 | 120.3; 126.4 |
| C—N(imine)-C(L) | 118.3; 119.3 | 120.3; 120.6 |
| Cl—Fe—Cl | 117.6 | 122.6 |

*B. L. Small and M. Brookhart J. Am. Chem Soc., v. 120 (1998) 4049. (Comparative)

The catalysts of the present invention can be advantageously used in copolymerization of ethylene with propylene or hexene-1. They show moderate activities in homopolymerization of propylene to yield polypropylene of moderate tacticity.

In the following examples, all synthetic procedure of catalysts preparation were carried out under argon atmosphere. All operations with catalysts samples and aluminum alkyls were carried out in a glove box under nitrogen.

EXAMPLE 1

Preparation of Cs Symmetric Iron Complex (1) Preparation of terphenylamine 2,6-Dibromoaniline (6.02 g, 24 mmol) and Pd(PPh$_3$)$_4$ (3.88 g, 3.00 mmol) were dissolved in toluene (240 ml). Phenyl boronic acid (8.80 g, 72 mmol) in EtOH (50 ml) was added. Na$_2$CO$_3$ (13 g, 144 mmol) in H$_2$O (70 ml) was added. The reaction mixture was reflux for 24 hrs. The organic layer was thin separated and the amine precipitated as hydrochloride salt by addition of 20 ml of HCl. The precipitate was isolated. The salt was suspended in ether, and 2 M Na$_2$CO$_3$ was added. The organic layer was dried over Na$_2$SO$_4$ and the solvent was evaporated. The yield was 90%. $^1$H NMR (CDCl$_3$): δ 7.44 (t, 4H, H$_{arom}$), 7.39 (t, 4H, H$_{arom}$), 7.29 (d, 2H, H$_{arom}$), 7.07 (d, 2H, H$_{arom}$), 6.82 (t, 1H, H$_{arom}$), 3.77 (s, 2H, NH$_2$).

(2) Preparation of ligand precursor: 2-acetyl-6-[1-(2,6-diphenyl phenylimino)ethyl]pyridine (monoimine Ph$_2$)

Diacethylpyridine (1.10 g, 6.7 mmol), terphenylamine (1.60 g, 6.7 mmol) and a catalytic amount of p-toluenesulfonic acid monohydrate in benzene (50 ml) were heated under reflux for 3 hrs. The product was crystallized from solution and washed with pentane to provide a yield of 1.6 g. According to GC and NMR analysis, the solid contained 85% monoimine and 15% bis-imine. After double crystallization from CH$_2$Cl$_2$/pentane (1:3), monoimine and bisimine were separated. Monoimine (Ph$_2$): $^1$H NMR (CDCl$_3$): δ 8.13 (d, 1H, H$_{pyr}$) 7.97 (d, 1H, H$_{pyr}$), 7.78 (t, 1H, H$_{pyr}$) 7.5–7.1 (m, 13H, H$_{arom}$), 2.59 (s, 3H, CH$_3$), 1.88 (s, 3H, CH$_3$). $^{13}$C NMR (CDCl$_3$): δ 166.2, 155.0, 152.1, 146.4, 140.1, 136.9, 131.8, 129.6, 129.2, 127.8, 126.6, 124.3, 124.2, 122.1, 25.2, 17.6.

(3) Preparation of ligand: 2-[1-(2,6-diisopropylphenylimino(ethyl]-6-[1-(2,6-diphenyl phenylimino)ethyl]pyridine (bis-imine i-Pr$_2$, Ph$_2$)

The monoimine (Ph$_2$) (0.70 g, 1.79 mmol), 2,6-di-isopropylaniline (0.70 g) and a catalytic amount of p-toluenesulfonic acid monohydrate in benzene (30 ml) were heated under reflux for two days. The solvent was removed under the vacuum. Double crystallization CH$_2$Cl$_2$/pentane (1:3) gave bis-imine (i-Pr$_2$,Ph$_2$) (0.38 g). $^1$H NMR (CDCl$_3$): δ 8.31 (d, 1H, H$_{pyr}$) 8.07 (d, 1H, H$_{pyr}$), 7.77 (t, 1H, H$_{pyr}$), 7.5–7.0 (16H, H$_{arom}$), 2.70 (sept, 2H, CH(CH$_3$)$_2$), 2.07 (s, 3H, CH$_3$—C=N), 1.89 (s, 3H, CH$_3$—C=N), 1.13 (t, 12H, CH(CH$_3$)$_2$).

(4) Preparation of iron complex: 2-[1-(2,6-diisopropylphenylimino(ethyl]-6-[1-(2,6-diphenyl phenylimino)ethyl]pyridine iron dichloride The bis-imine (i-Pr$_2$, Ph$_2$) (0.38 g, 0.69 mmol) and iron dichloride (II) (90.0 mg) in THF (10 ml) were stirred for night at 30° C. The solvent was removed under the vacuum. The compound was crystallized from methylene chloride/pentane. Yield: 0.40 g.

EXAMPLE 2

Preparation of Cs Symmetric Iron Complex (1) Preparation of ligand: 2-[1-(2,4,6-trimethylphenylimino(ethyl]-6-[1-(2,6-diphenyl phenylimino)ethyl]pyridine (bis-imine Me3, Ph2)

The same procedure as in Example 1(3) was repeated except that reaction was conducted by using the monoimine (Ph$_2$) (1.39 g, 3.56 mmol) and 2,4,6-dimethylaniline (1.5 g, 11.1 mmol). $^1$H NMR (CD$_2$Cl$_2$): δ 8.33 (d, 1H, H$_{pyr}$), 8.10 (d, 1H, H$_{pyr}$) 7.81 (t, 1H, H$_{pyr}$), 7.6–6.9 (15H, H$_{arom}$), 2.19 (s, 3H, CH$_3$ from Ph), 2.14 (s, 6H, CH$_3$ from Ph), 2.06 (s, 3H, CH$_3$—C=N), 1.92 (s, 3H, CH$_3$—C=N).

(2) Preparation of iron complex: 2-[1-(2,4,6-trimethylphenylimino (ethyl]-6-[1-(2,6-diphenyl phenylimino) ethyl]pyridine iron dichloride The same procedure as in Example 1(4) was repeated except that reaction was conducted by using bis-imine (Me$_3$,Ph$_2$) instead of bis-imine (i-Pr2, Ph2). As a result, 0.39 grams of 2-[1-(2,4,6-trimethylphenylimino(ethyl]-6-[1-(2,6-diphenylphenylimino)ethyl]pyridine iron dichloride were obtained.

EXAMPLE 3

Preparation of Cs Symmetric Iron Complex (1) Preparation of ligand: 2-[1-(2,6-dimethylphenylimino (ethyl]-6-[1-(2,6-diphenyl phenylimino)ethyl]pyridine (bis-imine Me$_2$, Ph$_2$)

Monoimine (Ph$_2$) (1.70 g, 4.36 mmol), 2,6-dimethylaniline (2.3 g) and a catalytic amount of p-toluenesulfonic acid monohydrate in benzene (30 ml) were heated under reflux overnight. The solvent was removed under the vacuum. Double crystallization CH$_2$Cl$_2$/pentane (1:3) gave bisimine (Me$_2$,Ph$_2$). (0.33 g). $^1$H NMR (CDCl$_3$): δ 8.34 (d, 1H, H$_{pyr}$), 8.08 (d, 1H, H$_{pyr}$) 7.77 (t, 1H, H$_{pyr}$), 7.5–6.9 (16H, H$_{arom}$), 2.06 (s, 3H, CH$_3$—C=N), 2.00 (s, 6H, CH$_3$), 1.89 (s, 3H, CH$_3$—C=N).

(2) Preparation of iron complex: 2-[1-(2,6-dimethylphenylimino(ethyl]-6-[1-(2,6-diphenylphenylimino)ethyl]pyridine iron dichloride The same procedure as in Example 1(4) was repeated except that reaction was conducted by using the bis-imine (Me$_2$,Ph$_2$) (0.33 g) and FeCl$_2$ (84.5 mg) instead of bis-imine (i-Pr$_2$, Ph$_2$). As a result, 0.35 grams of 2-[1-(2,6-dimethylphenylimino (ethyl]-6-[1-(2,6-diphenyl phenylimino) ethyl]pyridine iron dichloride were obtained.

EXAMPLE 4

Preparation of Cs Symmetric Iron Complex (1) Preparation of 2,6-Bis(4-t-butylphenyl)aniline The same procedure as in Example 1(1) was used except that reaction was conducted by using 2,6-dibromoaniline (9.00 g, 35.6 mmol), Pd(PPh$_3$)$_4$ (5.0 g), and 4-t-butylphenyl boronic acid (19.0 g, 107 mmol). Yield 3.0 g. $^1$H NMR (CD$_2$Cl$_2$): δ 7.50 (d, 4H, H$_{arom}$), 7.43 (d, 4H, H$_{arom}$), 7.08 (d, 2H, H$_{arom}$), 6.83 (t, 1H, H$_{arom}$), 3.93 (s, 2H, NH$_2$), 1.38 (s, 18H, t-Bu).

(2) Preparation of ligand precursor: 2-acetyl-6-[1-(2,6-bis(4-t-butylphenyl)imino)ethyl]pyridine (monoimine (t-BuPh$_2$))

The same procedure as in Example 1(2) was used except that reaction was conducted by using diacethylpyridine (0.64 g, 3.93 mmol) and 2,6-di(t-butylphenyl)aniline (1.41 g, 3.95 mmol). The yield was 0.95 g of the monoimine (t-BuPh$_2$): $^1$H NMR (CD$_2$Cl$_2$): δ 8.20 (d, 1H, H$_{pyr}$), 8.00 (d, 1H, H$_{pyr}$), 7.85 (t, 1H, H$_{pyr}$) 7.5–7.2 (m, 11H, H$_{arom}$), 2.61 (s, 3H, CH$_3$), 1.94 (s, 3H, CH$_3$), 1.30 (s, 18H, t-Bu).

(3) Preparation of ligand: 2-[1-(2,6-dimethylphenylimino(ethyl]-6-[1-(2,6-bis(4-t-butylphenyl)imino)ethyl]pyridine (bis-imine Me2, t-BuPh2)

The same procedure as in Example 3(2) was used except that reaction was conducted by using monoimine (t-BuPh$_2$) (1.30 g), 2,6-dimethylaniline (1.40 g). The yield was 0.55 g.

(4) Preparation of iron complex: 2-[1-(2,6-dimethylphenylimino(ethyl]-6-[1-(2,6-bis(4-t-butylphenyl)imino)ethyl]pyridine iron dichloride The same procedure as in Example 1(4) was repeated except that reaction was conducted by using the bis-imine (Me$_2$,t-BuPh$_2$) (0.45 g) and FeCl$_2$ (94.5 mg). The yield was 0.40 g.

EXAMPLE 5–13

Ethylene Polymerization/Copolymerization in a Bench Reactor at 80° C.

Table 2 sets forth the ethylene polymerization/copolymerization conditions and the yields and activities for the catalysts as indicated in the table. The bench reactor parameters for all tests were as follows: i-butane (1,200 g), 8% of ethylene, temperature 80° C., MAO to provide Fe/Al ratio of 1:1000.

TABLE 2

| Ex. | Catalyst | Amount, mg | Time, min | H2 | Hexene-1 | Yield, g | Activity, g PE/gCat/h |
|---|---|---|---|---|---|---|---|
| 5 | Me2,t-BuPh2 (from ex. 4) | 1.0 | 60 | 0 | 0 | 322 | 322,000 |
| 6 | Me2,t-BuPh2 (from ex. 4) | 0.5 | 26 | 0 | 0 | 259 | 1,195,385 |
| 7 | Me2,t-BuPh2 (from ex. 4) | 0.5 | 30 | 0.5 L | 0 | 160 | 640,000 |
| 8 | Me2,t-BuPh2 (from ex. 4) | 0.5 | 30 | 0 | 40 ml | 80 | 320,000 |
| 9 | (Me3)(Ph2) (from ex. 2) | 0.5 | 30 | 0 | 0 | 39 | 156,000 |
| 10 | (Me3)(Ph2) (from ex. 2) | 0.5 | 30 | 0.5 L | 0 | 46 | 184,000 |
| 11 | (Me3)(Ph2) (from ex. 2) | 0.5 | 30 | 0.5 L | 40 ml | 54 | 216,000 |
| 12 | (Me3)(Ph2) (from ex. 2) | 0.5 | 30 | 0 | 40 ml | 18 | 72,000 |
| 13 | (i-Pr2)(i-Pr2) Comparative | 2.0 | 60 | 0 | 0 | 202 | 62,825 |

Table 3 sets forth properties of polymers produced in Examples 6–12.

TABLE 3

| Catalyst Example | (Me2)(tBuPh) 6 | (Me2)(tBuPh),H2 7 | (Me2)(tBuPh),C6 8 | (Me3)(Ph2) 9 | (Me3)(Ph2) H2 10 | (Me3)(Ph2) C6 12 | (Me3)(Ph2) H2 + C6 11 |
|---|---|---|---|---|---|---|---|
| Density | 0.9631 | 0.9626 | 0.9653 | | | | |
| Second Melt Peak C | 135.37 | 135.37 | 133.70 | | | | |
| MI2 (g/10 MIN) | 0.17 | 0.23 | 1.18 | | | | |
| MI5 (g/10 MIN) | 0.64 | 1.09 | 4.59 | | | | |
| HLMI (g/10 MIN) | 11.4 | 28.4 | 83.9 | | | | |

TABLE 3-continued

| Catalyst Example | (Me2)(tBuPh) 6 | (Me2)(tBuPh),H2 7 | (Me2)(tBuPh),C6 8 | (Me3)(Ph2) 9 | (Me3)(Ph2) H2 10 | (Me3)(Ph2) C6 12 | (Me3)(Ph2) H2 + C6 11 |
|---|---|---|---|---|---|---|---|
| SR5 (HLMI/MI5) | 17.8 | 26.1 | 18.3 | | | | |
| SR2 (HLMI/MI2) | 67.1 | 123.5 | 71.1 | | | | |
| Flow Activation Energy KJOLPERMOL | 27.8 | 31.0 | 29.7 | | | | |
| Zero Shear Viscosity (PASCAL/SEC) | 3.55E+05 | 4.49E+05 | 4.54E+04 | | | | |
| Relaxation Time (Sec) | 0.235 | 0.428 | 0.027 | | | | |
| Breadth Parameter | 0.203 | 0.187 | 0.194 | | | | |
| % Wax | 0.3 | 0.3 | 0.2 | | | | |
| Mw | 273,711 | 231,124 | 132,174 | 243,771 | 230,666 | 119,599 | 200,713 |
| D | 14.68 | 15.13 | 8.24 | 16.3 | 16.1 | 18.4 | 19.6 |
| D' | 9.02 | 10.24 | 9.48 | 9.3 | 11.1 | 10.5 | 14.3 |

EXAMPLES 14–16

Ethylene Polymerization/Copolymerization in the Bench Reactor at 50° C.

Table 4 sets forth ethylene polymerization/copolymerization conditions for the catalyst produced in Example 3. The bench reactor conditions were as follows: i-butane, 7% of ethylene, temperature 50° C., MAO to provide Fe/Al ratio of 1:1000.

TABLE 4

| Ex. | Catalyst | Amount, mg | Time, min | H2//C2 | Hexene-1, ml | Yield, g | Activity, g PE/gCat/h |
|---|---|---|---|---|---|---|---|
| 14 | Me$_2$,Ph$_2$ (from ex. 3) | 2.0 | 60 | 0 | 0 | 29 | 8,900 |
| 15 | Me$_2$,Ph$_2$ (from ex. 3) | 2.0 | 60 | 0.006 | 0 | 35 | 10,850 |
| 16 | Me$_2$,Ph$_2$ (from ex. 3) | 2.0 | 60 | 0 | 30 | 14 | 4,340 |

EXAMPLE 17

Propylene Polymerization

The polymerization of propylene was carried out with 3 mg of the Me$_2$Ph$_2$ catalyst from Example 3, MAO (0.2 ml, 30% in toluene) in 50 ml of toluene at −10° C. for 3 hours under 1 atm of propylene. 0.20 g of polypropylene was isolated. The polypropylene was moderately isotactic as indicated by the following pentad distribution from $^{13}$C NMR analysis: (%) mmmmm 55.3, mmmr 16.3, mmrr 4.9, xmrx 17.1, mrrm 1.5.; % mesodiads 85.1, % racemic diads 14.9%.

The polymer products produced by the polymerization of ethylenically unsaturated monomers in accordance with the present invention, including ethylene homopolymers, C$_{3+}$ alpha olefin homopolymers and ethylene-C$_{3+}$ alpha olefin copolymers, such as ethylene propylene copolymers, can be used to produce a wide variety of end use products. Thus, the polymer products may be employed to produce blow-molded products or injection-molded products, such as bottles for milk, food, and detergents and the like, house-wares, such as toys and pails and various extruded products. Such extruded products include film products for producing grocery and merchandise bags, packaging for food products, sheets for truck bed liners and luggage, shipping containers and bulk storage tanks. Large blow molded parts which can be produced include articles such as shipping containers and bulk storage tanks, and pipes, including high pressure pipes for use in various industrial applications such as for sewer pipes and pipes for gas, oil, and water transport applications. The polyethylene products are characterized by a high electrical resistivity and thus may be used in insulating applications such as insulating coatings on electrical wiring products. Molded ethylene homopolymer or copolymer products produced in accordance with the present invention can also be used to provide various automotive components by injection moldings, including, without limitation, automobile or truck dashboards and interior trim moldings. Where the polymer products produced in accordance with the present invention are used to make end use products by injection molding, various injection molded components may be made by injecting the polymer product into molds conforming to the shape of the article to be manufactured. As indicated, various articles may also be produced by blow molding to produce containers, bottles and the like, or by extrusion to form thin film products. In addition to films and the like, the ethylene homopolymer or copolymer product produced by the process of the present invention may be used to produce various fibers, meshes and textile materials as well as articles of apparel, such as gowns, masks, gloves and the like.

Having described specific embodiments of the present invention, it will be understood that modifications thereof may be suggested to those skilled in the art, and it is intended to cover all such modifications as fall within the scope of the appended claims.

The invention claimed is:

1. An olefin polymerization catalyst precursor composition comprising a C$_s$ symmetric catalyst precursor characterized by the formula:

wherein M is a transition metal selected from groups 8 to 10 of the Periodic Table; n is an integer of from 1 to 3; Q is a halogen or a $C_1$ to $C_2$ alkyl group; PY is a pyridinyl group, which are coordinated with M through the nitrogen atom of said pyridinyl group; R' is a $C_1$ to $C_{20}$ hydrocarbyl group; R" is a $C_1$ to $C_{20}$ hydrocarbyl group; $A_1$ is a monoaromatic group, which are substituted or unsubstituted; and $A_2$ comprises multiple aromatic groups, which are substituted or unsubstituted, wherein the C=N bonded groups are excluded from $A_1$ and $A_2$.

2. The composition of claim 1, wherein R' is a $C_1$–$C_4$ alkyl group or an aryl group which is substituted or unsubstituted and R" is a $C_1$–$C_4$ alkyl group or an aryl group which is substituted or unsubstituted.

3. The composition of claim 1 wherein M is iron or cobalt and n is 2.

4. The composition of claim 1, wherein $A_1$ is an unsubstituted phenyl group or a mono-substituted, di-substituted or tri-substituted phenyl group.

5. The composition of claim 4 wherein $A_1$ is a phenyl group which is mono-substituted at the para position.

6. The composition of claim 4 wherein $A_1$ is a di-substituted phenyl group substituted at the ortho positions with $C_1$–$C_4$ alkyl groups or is a tri-substituted phenyl group substituted with a $C_1$–$C_4$ alkyl group at the para position and $C_1$–$C_4$ alkyl groups at the ortho positions.

7. The composition of claim 6 wherein $A_2$ is a terphenyl group which is substituted or unsubstituted.

8. The composition of claim 7 wherein $A_2$ is a terphenyl group wherein the substituent phenyl groups are substituted on the primary phenyl group at the ortho positions with respect to the coordinating nitrogen ion.

9. The composition of claim 8 wherein both of the substituent phenyl groups of $A_2$ are substituted at the para positions with $C_1$–$C_4$ alkyl groups.

10. An olefin polymerization catalyst precursor composition comprising a $C_s$ symmetric catalyst component characterized by the formula:

wherein Q is a halogen or a $C_1$–$C_2$ alkyl group; $R_1$ is a hydrogen or a methyl group; $R_2$ is a methyl or isopropyl group; and $R_4$ is a $C_1$–$C_4$ alkyl group.

11. The composition of claim 10, wherein $R_4$ has a higher molecular weight than $R_2$.

12. The composition of claim 10, wherein $R_2$ is a methyl group.

13. The composition of claim 12 wherein $R_4$ is an isopropyl or tertiary butyl group.

14. The composition of claim 13 wherein $R_4$ is a tertiary butyl group.

15. The composition of claim 14 wherein Q is chlorine.

16. The composition of claim 15 wherein $R_1$ is a methyl group.

17. An olefin polymerization catalyst precursor composition comprising a $C_s$ symmetric catalyst component characterized by the formula:

wherein Q is a halogen or a $C_1$–$C_2$ alkyl group; $R_1$ is a H or $C_1$–$C_4$ alkyl group; $R_2$ is a $C_1$–$C_4$ alkyl group; $R_3$ is hydrogen or a $C_1$–$C_4$ alkyl group; $R_5$ is hydrogen or a $C_1$–$C_4$ alkyl group which is the same as or different from $R_3$; $R_4$ is hydrogen or a $C_1$–$C_4$ alkyl group.

18. The composition of claim 17, wherein $R_2$ is an isopropyl group.

19. The composition of claim 18 wherein $R_4$ is hydrogen.

20. The composition of claim 17, wherein Q is chlorine.

* * * * *